(12) United States Patent
Hsieh et al.

(10) Patent No.: US 8,367,015 B2
(45) Date of Patent: Feb. 5, 2013

(54) ANALYTICAL STRIP AND THE MANUFACTURING METHOD THEREOF

(75) Inventors: Wen-Pin Hsieh, Hsinchu (TW);
Ching-Tai Tseng, Hsinchu (TW);
Jui-Tse Chen, Hsinchu (TW)

(73) Assignee: Actherm Inc, Hsinchu (TW)

( * ) Notice: Subject to any disclaimer, the term of this patent is extended or adjusted under 35 U.S.C. 154(b) by 324 days.

(21) Appl. No.: 12/762,165

(22) Filed: Apr. 16, 2010

(65) Prior Publication Data

US 2010/0240120 A1 Sep. 23, 2010

(30) Foreign Application Priority Data

Mar. 23, 2009 (WO) ................ PCT/CN2009/070941

(51) Int. Cl.
*G01N 21/75* (2006.01)
(52) U.S. Cl. ...................................................... 422/417
(58) Field of Classification Search .................... 422/417
See application file for complete search history.

(56) References Cited

U.S. PATENT DOCUMENTS

| | | | |
|---|---|---|---|
| 4,828,801 A | 5/1989 | Lombardy wife Alric et al. | |
| 5,290,518 A * | 3/1994 | Johnson | 422/413 |
| 5,837,584 A | 11/1998 | Lu et al. | |
| 6,210,907 B1 | 4/2001 | Cha | |
| 6,670,115 B1 | 12/2003 | Zhang | |
| 6,756,019 B1 | 6/2004 | Dubrow et al. | |
| 7,455,816 B2 | 11/2008 | Steuer et al. | |
| 8,124,029 B2 * | 2/2012 | Polwart et al. | 422/502 |
| 2002/0048533 A1 * | 4/2002 | Harms et al. | 422/99 |
| 2006/0051248 A1 * | 3/2006 | Cho et al. | 422/100 |
| 2006/0188395 A1 | 8/2006 | Taniike et al. | |
| 2006/0285996 A1 | 12/2006 | Ohman et al. | |
| 2007/0059488 A1 | 3/2007 | Aizenberg et al. | |
| 2007/0092411 A1 * | 4/2007 | Leach et al. | 422/101 |
| 2008/0019866 A1 | 1/2008 | Paek et al. | |
| 2008/0108096 A1 | 5/2008 | Peter | |
| 2008/0194804 A1 | 8/2008 | Chang et al. | |

FOREIGN PATENT DOCUMENTS

| | | |
|---|---|---|
| CN | 1139982 A | 1/1997 |
| CN | 1146557 A | 4/1997 |
| CN | 1309294 A | 8/2001 |
| CN | 1334924 A | 2/2002 |
| CN | 1407339 A | 4/2003 |
| CN | 1429337 A | 7/2003 |
| CN | 1519563 A | 8/2004 |
| CN | 1830390 A | 9/2006 |
| CN | 1851459 A | 10/2006 |
| CN | 1854728 A | 11/2006 |
| CN | 1954214 A | 4/2007 |
| CN | 101021631 A | 8/2007 |
| CN | 101303358 A | 11/2008 |
| JP | 2007139649 A | 6/2007 |
| TW | 200739075 | 10/2007 |
| TW | M350706 | 2/2009 |

(Continued)

*Primary Examiner* — Lore Jarrett
(74) *Attorney, Agent, or Firm* — Ming Chow; Sinorica, LLC (57) ABSTRACT

An analytical strip including a substrate and a channel structure is disclosed. A substrate has a flat surface and the channel is formed on the flat surface according to a predetermined pattern. The surface of channel structure is not lower than the surface of the substrate. The channel has a hollow-matrix conformation and the channel is more hydrophilic than the flat surface of the substrate is. The strip also contains a reaction material formed in the hollow-matrix.

18 Claims, 7 Drawing Sheets

FOREIGN PATENT DOCUMENTS

| | | |
|---|---|---|
| TW | M354070 | 4/2009 |
| TW | M359693 | 6/2009 |
| WO | WO9008322 A1 | 7/1990 |
| WO | WO0042434 A1 | 7/2000 |
| WO | WO0184153 A1 | 11/2001 |
| WO | WO2004086042 A1 | 10/2004 |
| WO | WO2006047869 A1 | 5/2006 |
| WO | WO2007081330 A1 | 7/2007 |
| WO | WO2007128286 A1 | 11/2007 |

* cited by examiner

ANALYTICAL STRIP AND THE MANUFACTURING METHOD THEREOF

BACKGROUND OF THE INVENTION

1. Technical Field

The present invention relates to analytical strips and more particularly, to an analytical strip for biochemical and immunological assays.

2. Description of Related Art

Analytical strips are conventionally used in biochemical tests and immunological tests. A typical analytical strip has a substrate or a base formed with sunken channels or microchannels and processed with hydrophobic and hydrophilic surface treatment. Since the channels are bordered by non-absorbent material, and fluid samples to be tested are usually viscous compositions containing, for example, protein or carbohydrate, a fluid sample flowing in the channels tends to adhere to surfaces of the channels and cannot be fully reacted. Consequently, the fluid sample is wasted, if not leading to errors of test results.

In addition, the conventional analytical strips are provided with micro-channels to facilitate fluid delivery, in which the micro-channels cause a capillary action that draws a fluid sample through the channels to a reaction/detection region. Alternatively, a fluid sample may be introduced into the channels with a driving force provided by, for example, a pressurizing means or a vacuum- or negative pressure-generating means, thereby propelling the fluid sample through the channels. Another approach to promoting fluid delivery is to provide the channels with one or more micro-actuators or micro-valves through which a fluid sample will pass successively before arriving at a reaction/detecting region. However, in any of the aforesaid approaches, air bubbles of various sizes tend to be generated in, or entrained into, fluid samples to be tested after the samples are introduced into the channels. These bubbles, when causing channel blockage, may result in test errors or even test failure. Moreover, installation of the micro-actuators or micro-valves will add to the overall difficulty of design and the cost of analytical strips.

Besides, during manufacture of the conventional analytical strips, the channels or microfluidic-channels are usually formed on the substrates by micro-injection forming or imprinting, using expensive die making process such as micro-machining or LIGA (abbreviation of "Lithographie GalVanoformung Abformung", or "Lithography Electroforming Micro Molding" in English) which, coupled with early wear and tear of molds, increases the total cost incurred in making analytical strips.

Hence, the residual of the fluid sample in the channel renders testing inconvenient and time-consuming. In addition, the manufacturing cost of traditional analytical strip is usually considerable.

SUMMARY OF THE INVENTION

In order to overcome the aforementioned shortcomings, the present invention provides an analytical strip comprising a substrate and a channel. The substrate has a flat surface and the channel is formed on the flat surface in a predetermined pattern. The surface of the channel is not lower than the surface of the substrate. The channel has a hollow-matrix conformation and the channel is more hydrophilic than the flat surface of the substrate is. The strip also contains a reaction material formed in the hollow-matrix.

Hence, the primary object of the present invention is to provide an analytical strip comprising the channel with hollow-matrix conformation. The channel thus has lower residual of samples in contrast to the traditional microfluidic channel, and low volume of samples needed for multi-analytes detection in a test is realized.

Another object of the present invention is to provide an analytical strip that comprises absorptive nitrocellulose layers having a constant volumetric absorptive capacity and thus allows a quantitative assay to be conducted via controlling the volume of the nitrocellulose layers.

Still another object of the present invention is to provide an analytical strip that has absorptive nitrocellulose layers with a hollow-matrix configuration, which is capable of destroying the air bubbles in the fluid sample when the fluid sample flows through the hollow matrix, as well as preventing the bubbles from blocking the channel or the microfluidic channel of the substrate. Thus, an accurate result of the quantitative assay could be assured.

Yet another object of the present invention is to provide an analytical strip comprising the channel formed on the flat surface of the substrate in the predetermined pattern, instead of using molding, injection forming, imprint or using expensive die making process such as micro-machining or lithography-electroforming-micro-molding, thus saving costs for mass manufacture of the analytical strip.

A further object of the present invention is to provide a manufacturing method that can produce an analytical strip of a reduced manufacturing cost and an improved measuring accuracy.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings.

DETAILED DESCRIPTION OF THE PREFERRED EMBODIMENTS

While the present invention proposes an analytical strip and the manufacturing method thereof, the physical and chemical principles as well as solution applying technology implemented therein have been known to one skilled in the art and need not to be discussed at any length herein. Meanwhile, the accompanying drawings referred to in the following description are provided for illustrative purposes and need not to be made to scale Please refer to FIG. 1A for an analytical strip according to the first embodiment of the present invention. The analytical strip 1 includes a substrate 10 and a channel structure 11. The substrate 10 has a flat surface 100, and the channel 11 is formed on the flat surface 100 of the substrate 10 according to a predetermined pattern 12. The surface of the channel 11 is not lower than the flat surface 100 of the substrate 10. In addition, the channel 11 has a hollow-matrix conformation and the channel 11 is more hydrophilic than the flat surface 100 of the substrate 10 is. For making the channel 11, a high-hydrophilic solution is applied to the flat surface 100 of the substrate 10 by means of lithographic printing, photogravure, anastatic printing, screen-printing, line marking, inkjet/spray, casting, or dipping.

Figure 1A:
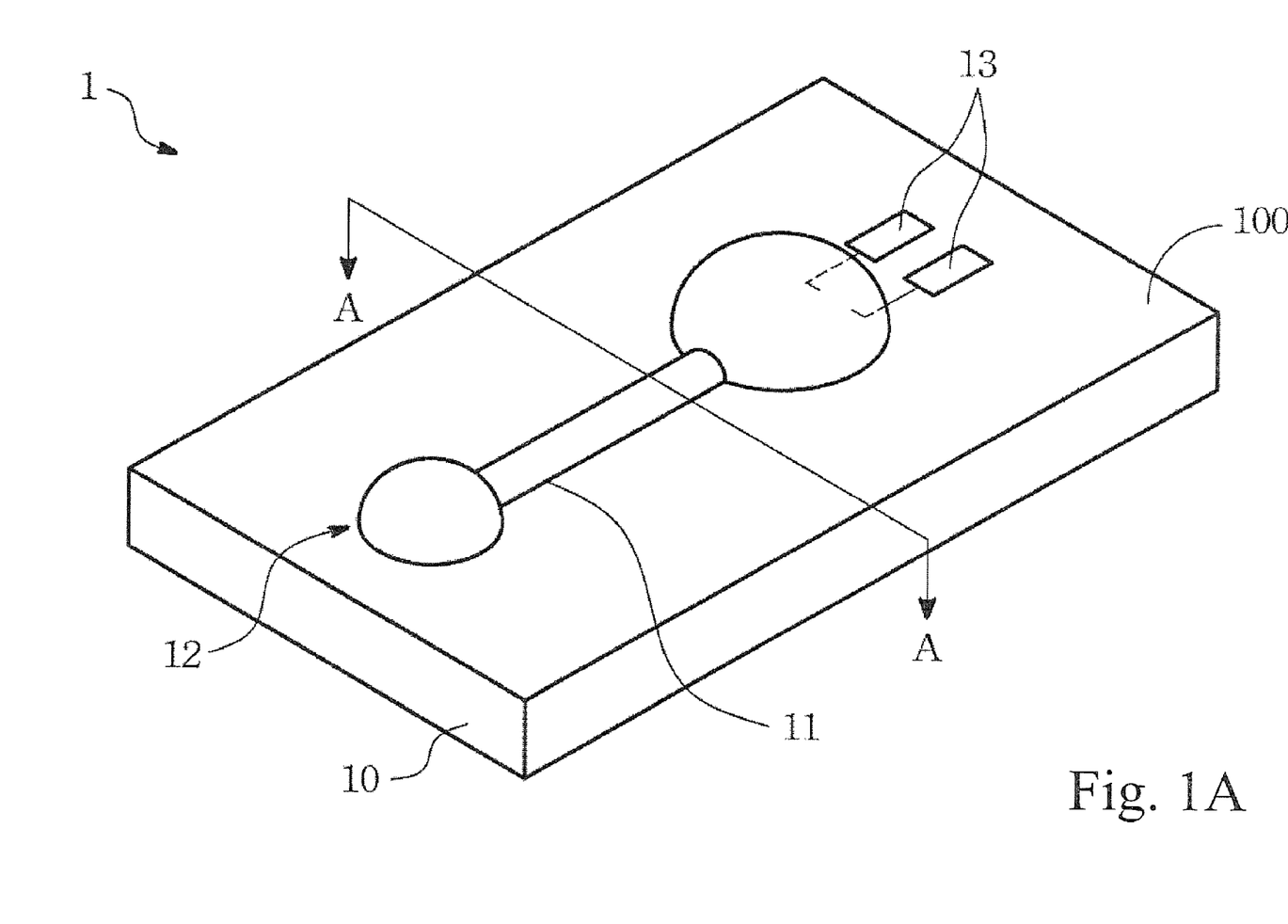
FIG. 1A is a schematic drawing of an analytical strip according to the first embodiment of the present invention.

The solution that is applied to the flat surface 100 of the substrate 10 may contains nitrocellulose or fiberglass, so that after dried and solidified the channel 11 is formed with porous hollow-matrix conformation therein to absorb the fluid sample to be tested, thereby minimizing the residual of the fluid sample in the channel 11. In addition, when the fluid sample passes along the channel 11, the hollow-matrix conformation will destroy the air bubbles in the fluid sample, thereby preventing the bubbles from blocking the channel 11. Moreover, the analytical strip 1 of the present invention further includes a pair of planar electrodes 13 disposed between the flat surface 100 of the substrate 10 and the channel 11, for detecting the electric signal produced by the electrochemical reaction of the fluid sample. Preferably, the substrate 10 is made of a flexible biocompatible material.

Accordingly, the channel 11 can be alternatively made by a needle pen that applies or injects the nitrocellulose solution onto the substrate 10 directly to draw the channel 11 to form the predetermined pattern 12. The surface of the substrate 10 can be smooth or rough. The needle pen can move in a three-dimension (i.e. moving in the x-, y-, or z-axis) thereby to control the thickness, width, and length of the channel 11. When the rate of which the solution applied or injected by the needle pen is constant, it is applicable to apply a predetermined amount of the solution onto the substrate 10 by controlling the speed of moving of the needle pen.

Figure 1B:
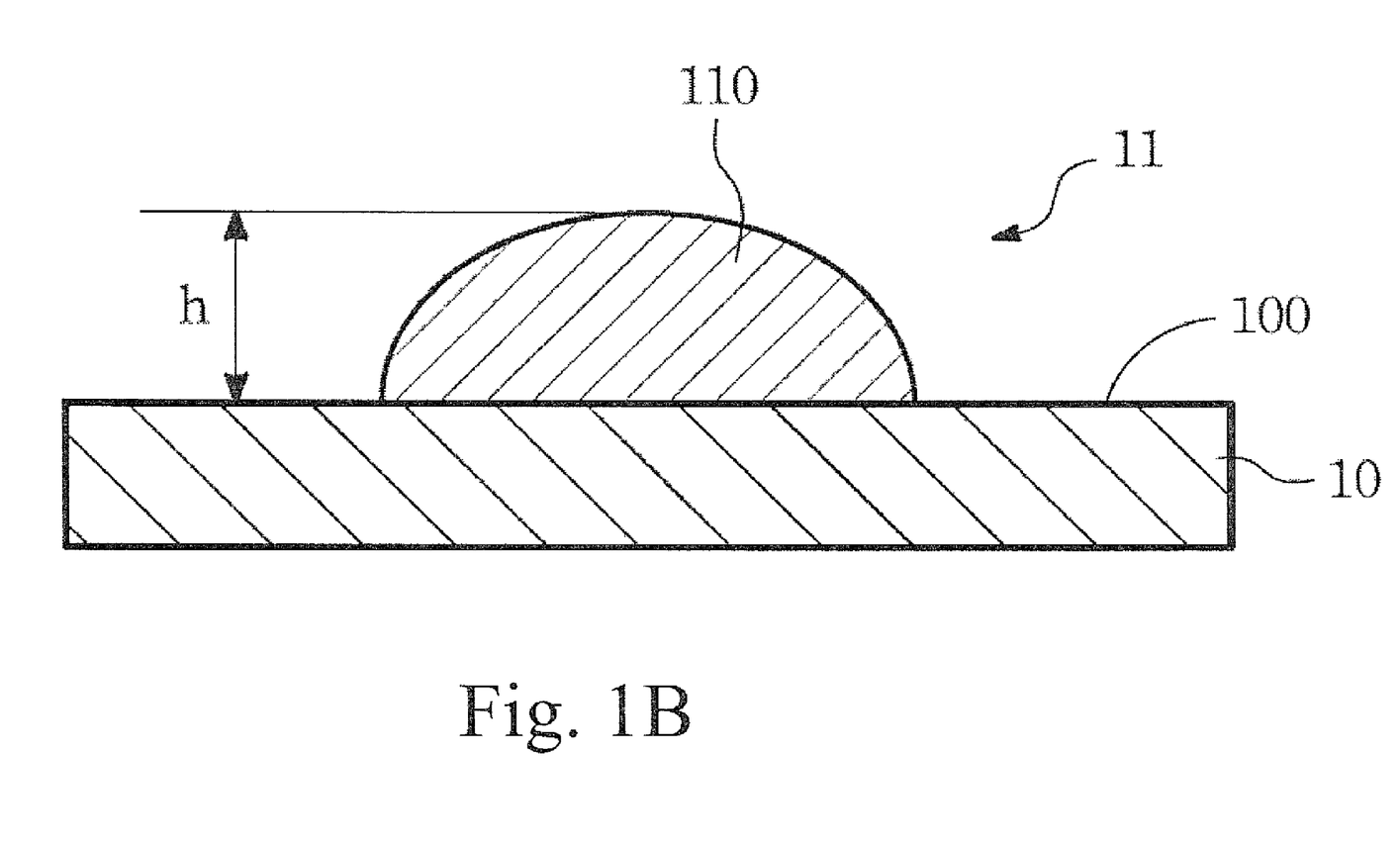
FIG. 1B is a sectional view of the analytical strip taken along Line AA of FIG. 1A.

Please refer to FIG. 1B for a sectional view of the analytical strip 1 taken along Line AA of FIG. 1A. During the drying and solidifying process of the nitrocellulose solution, the cohesion of the solution causes the channel 11 to rise from the flat surface 100 in a sectional respect thereof. Furthermore, since the channel 11 is formed on the flat surface 100 of the substrate 10, a height different h exists between the channel surface 110 and the flat surface 100 of the substrate 10. In other words, the channel surface 110 is not lower than the flat surface 100 of the substrate 10.

In addition, the hollow-matrix conformation of the channel 11 contains a reaction material, whose composition is associated with the substance to be tested in the fluid sample.

The solution for forming the channel 11 is prepared as following description. Nitrocellulose powder is mixed with an organic solvent containing ester and ketone to form a mixed solution. Alternatively, the mixed solution can be prepared by dissolving fiberglass in a specific solvent.

The mixed solution is then applied onto the flat surface 100 of the substrate 10 in a predetermined pattern. After the solution is dried, the resultant channel 11 has a hollow-matrix conformation that is fluid absorbing. Therefore, when the fluid sample is introduced into the analytical strip 1, the channel 11 with the hollow-matrix conformation can absorb and deliver the fluid sample to the reaction region (not shown) where the biochemical or immunological reaction is carried out.

In addition, since the channel 11 of the present embodiment is entirely of the hollow-matrix conformation and each volumetric unit of the channel 11 has a constant absorptive capacity, the volume of the mixed solution that is required to form the channel 11 can be derived from the desired volume of the fluid sample to be adsorbed and analyzed. As a result, the required volume of the fluid sample of the analytical strip 1 will be fixedly set, so that the resultant analytical strip 1 is suitable for an assay in a small volume.

The reaction material is preferably formed in the hollow-matrix conformation of the channel 11 as following description. After the mixed solution applied to the substrate 10 is dried and solidified to form the channel 11, a reaction solution containing the reaction material is injected to the channel 11, followed by air-drying or lyophilization. The reaction material dried in the channel 11 will be in the form of powder.

The analytical strip 1 of the present invention can be applied to either biochemical assays or immunological assay. To detect different analytes of the physiological fluid needs different assays, and different categories of assays require different kinds of reaction materials, which result in different categories of signals. A biochemical quantitative assay, for example, is usually carried out via the enzymatic reaction of the analytes in the biological fluid sample and a chemical luminating reagent, which is catalyzed by the suitable enzymes, to generate optical signals with specific wavelengths for detection. Accordingly, the reaction materials of the analytical strip 1, when applied to the biochemical quantitative assay, will mainly comprise enzymes and the corresponding chemical reagents. On the other hand, when the scenario comes to the quantitative detection of a certain protein in the physiological fluid sample, such as $\alpha$-fetoprotein, the analytical assay usually utilize an antibody that can specifically recognize the targeted protein and other corresponding chemical reagents to generate detectable signals. Accordingly, the reaction materials of the analytical strip 1, when applied to the quantitative immunoassay, will mainly comprise antibodies and the corresponding reagents. Therefore, the analytical strip 1 of the present invention is adaptive to quantitative detection of various analytes in different types of physiological fluidic specimens (e.g., urine or blood).

Figure 1C:
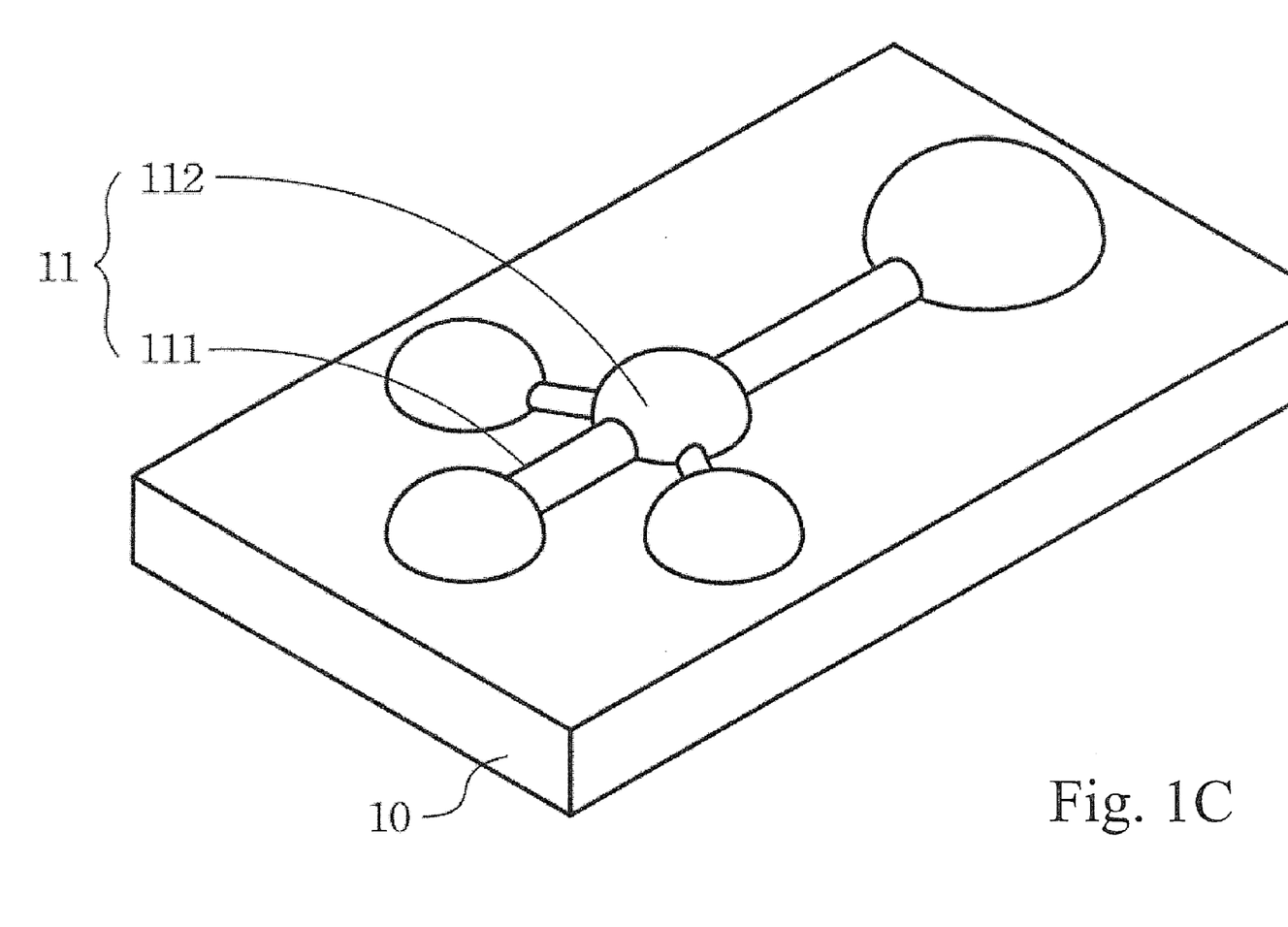
FIG. 1C is a schematic drawing of an analytical strip according to another mode of the first embodiment of the present invention.

FIG. 1C depicts another mode of the analytical strip disclosed in the present invention. The channel 11 may further comprise at least one branch channel 111 and an extended region 112 so that different fluids (such as the fluid sample to be tested and the reagent required for the reaction) can flow along different branch channel 111 and mix in the extended region 112 thoroughly. The extended region 112 may be shaped as a dome, an oblong or an island, so as to provide a sufficient reaction time for the fluid sample in the channels reacting with the reaction material, thereby improving accuracy of the result of the assay.

Figure 1D:
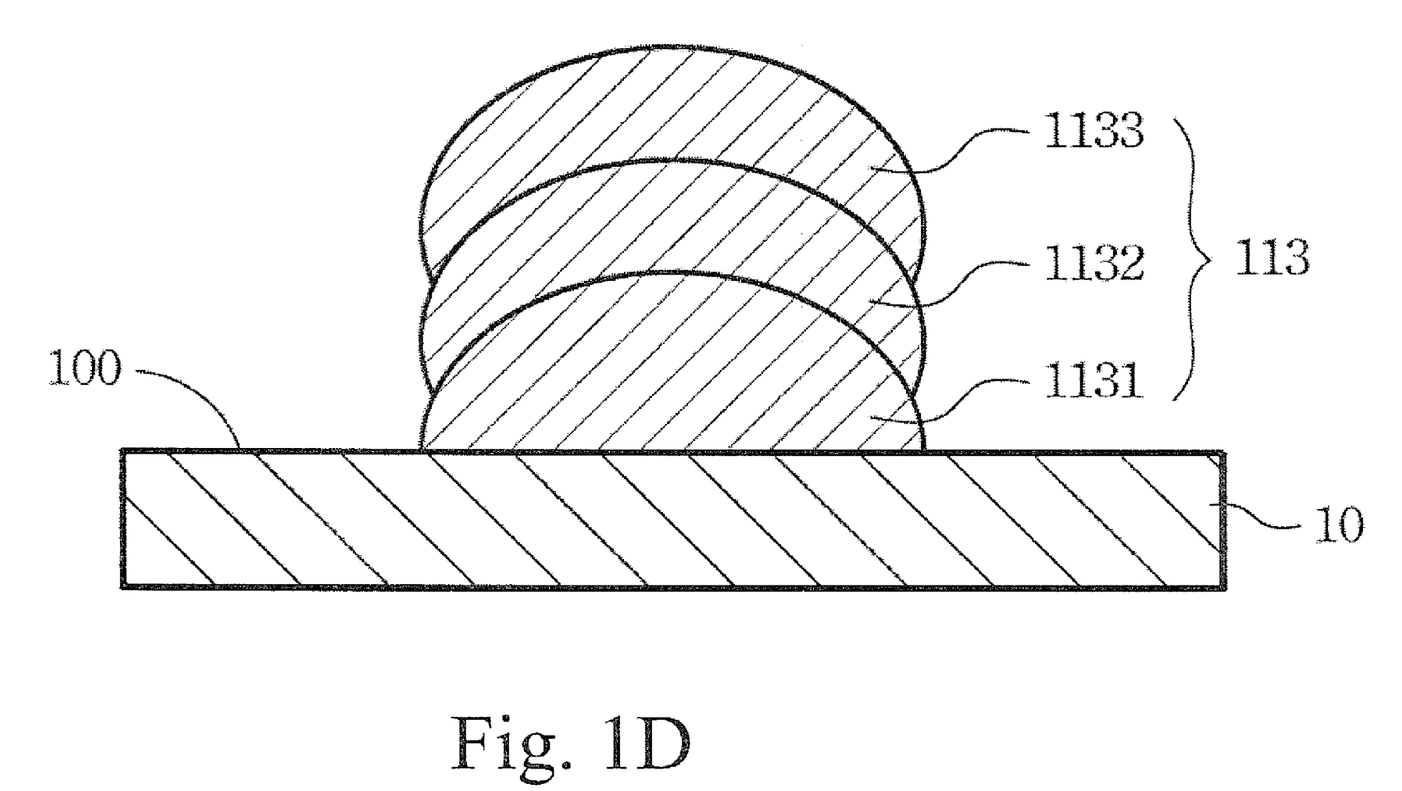
FIG. 1D is a schematic drawing of an analytical strip according to still another mode of the first embodiment of the present invention.

As shown in FIG. 1D, the flat surface 100 of the substrate 10 may further comprises a stacked channel 113. The stacked channel 113 comprises a first channel 1131, a second channel 1132, and a third channel 1133. In the stacked channel 113, the channels may be of the same or different channel patterns, according to the categories of the assays to be conducted and the fluid sample to be tested.

In addition to the aforementioned analytical strips of the first embodiment, the present invention also provides the manufacturing methods for making analytical strips, as the second and the third preferred embodiments described below.

Figure 2:
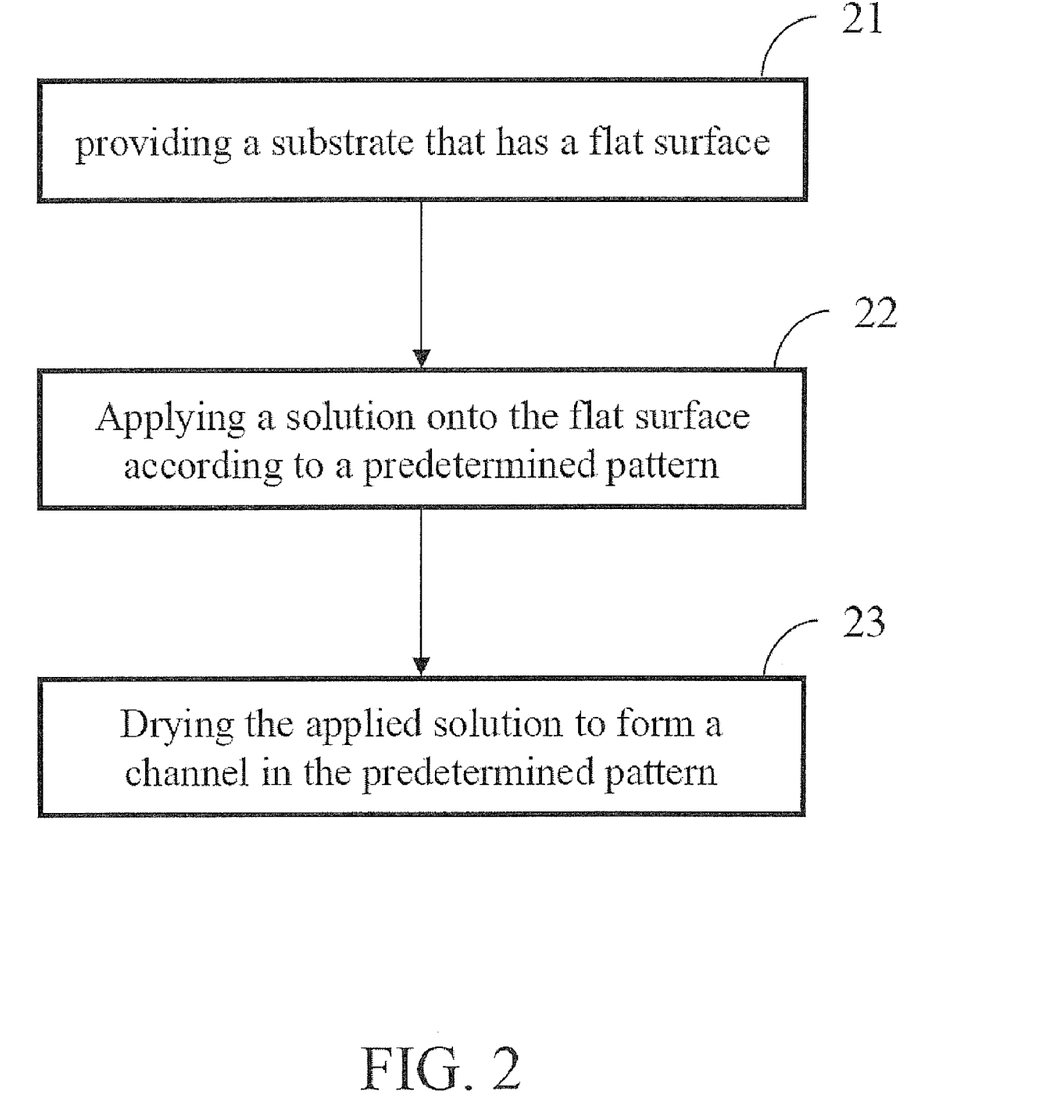
FIG. 2 is a flow chart of a manufacturing method of an analytical strip according to a second embodiment of the present invention.

Please refer to FIG. 2 for a flow chart of a manufacturing method of an analytical strip according to the second embodiment of the present invention. It is to be noted that the analytical strip mentioned in the present embodiment has the same structural features as those of the first embodiment while the same numerals as shown in FIGS. 1A through 1C are used herein without repeated explanation.

The manufacturing method of the analytical strip of this embodiment primarily comprises the following steps:

Step 21: Firstly providing a substrate 1 that has a flat surface 100;

Step 22: Applying a solution onto the flat surface 100 according to a predetermined pattern 12; and Step 23: Drying the applied solution to form a channel 11 with the predetermined pattern 12. A height difference h exists between the surface of the dried channel structure 11 and the substrate 10, and the solution may be applied by means of lithographic printing, photogravure, anastatic printing, screen printing, line marking or inkjet/spray.

Accordingly, the step 22 of applying the solution onto the flat surface can alternatively be using a needle pen that applies or injects the solution onto the substrate directly to draw the channel 11 to form the predetermined pattern 12. The surface of the substrate 10 can be smooth or rough. The needle pen can move in a three-dimension (i.e. moving in the x-, y-, or z-axis) thereby to control the thickness, width, and length of the channel 11. When the rate of which the solution applied or injected by the needle pen is constant, it is applicable to apply a predetermined amount of the solution onto the substrate 10 by controlling the speed of moving of the needle pen.

Figure 3A:
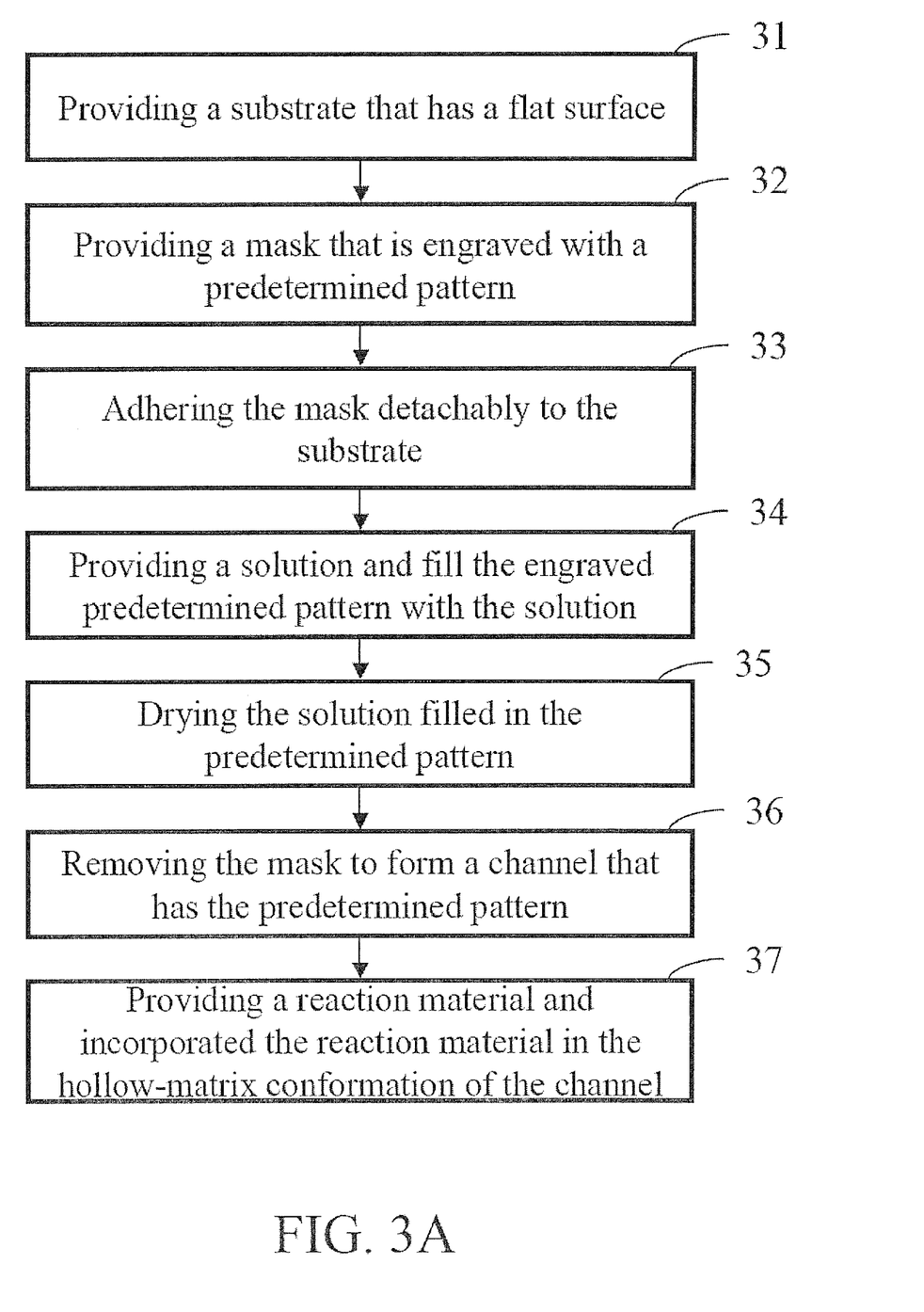
FIG. 3A is a flow chart of a manufacturing method of an analytical strip according to a third embodiment of the present invention.
Figure 3B:
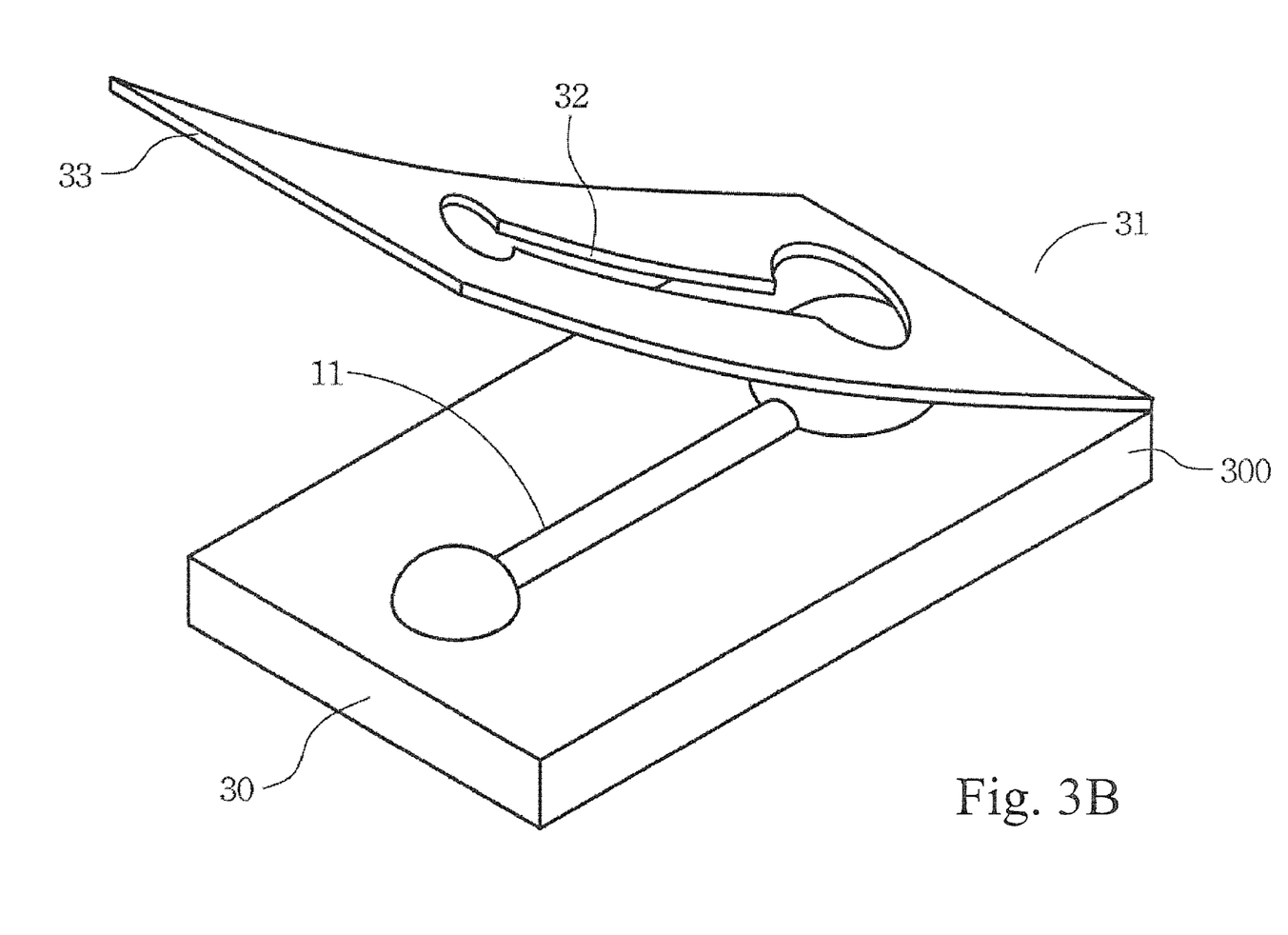
FIG. 3B is a schematic drawing of the analytical strip in the process of the manufacturing method according to the third embodiment of the present invention.

The third preferred embodiment of the present relates to an alternative manufacturing method of the analytical strip. Please refer to FIGS. 3A and 3B. FIG. 3A is a flow chart of the manufacturing method of the third embodiment of the present invention. FIG. 3B shows the analytical strip in the process of the manufacturing method of the present embodiment.

The manufacturing method of the analytical strip of the present embodiment primarily comprises the following steps:

Step 31: Firstly providing a substrate 30 that has a flat surface 300.

Step 32: Providing a mask 33 that is engraved with a predetermined pattern 32.

Step 33: Adhering the mask 33 detachably to the substrate 30.

Step 34: Providing a solution and fill the engraved predetermined pattern 32 with the solution.

Step 35: Drying the solution filled in the predetermined pattern 32.

Step 36: Removing the mask 33 to form a channel 31 that has the predetermined pattern 32. The surface of the dried channel 31 is not lower than the flat surface 300 of the substrate 30, and the channel 31 has a hollow-matrix conformation. In addition, the channel 31 is more hydrophilic than the flat surface 300 of the substrate 30 is.

Step 37: Providing a reaction material and incorporated the reaction material in the hollow-matrix conformation of the channel 31.

In the present embodiment, the formation of the channel 31, the composition of the solution and the way to incorporate the reaction material in the hollow-matrix conformation are similar to those described in the first embodiment and omitted herein.

The present invention has been described with reference to the preferred embodiment and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. An analytical strip comprising:
a substrate having a flat surface;
a channel formed on the flat surface, wherein a surface of the channel is higher than the flat surface of the substrate, the channel has a hollow-matrix conformation, and the channel is more hydrophilic than the flat surface of the substrate; and
a reaction material incorporated in the hollow-matrix conformation.

2. The analytical strip of claim 1, wherein the channel is made of a material selected from the group consisting of nitrocellulose and fiberglass.

3. The analytical strip of claim 1, wherein the channel further comprises a plurality of branch channels.

4. The analytical strip of claim 3, wherein at least one said branch channel further comprises an extended region that has a shape selected from the group consisting of a dome, an oblong and an island.

5. The analytical strip of claim 1, wherein the substrate is made of a material that is biocompatible.

6. The analytical strip of claim 1, wherein the substrate is flexible.

7. The analytical strip of claim 1, wherein the reaction material is selected from the group consisting of a chemical reagent, an enzyme reagent, and an antibody.

8. The analytical strip of claim 1, further comprising a pair of planar electrodes formed between the flat surface and the channel.

9. The analytical strip of claim 1, further comprising a stacked channel formed on the channel.

10. A manufacturing method of an analytical strip, comprising:
providing a substrate having a flat surface;
applying a solution onto the flat surface;
drying the applied solution to form a channel, in a manner that a surface of the channel is higher than the flat surface, and the channel has a hollow-matrix conformation, wherein the channel is more hydrophilic than the flat surface of the substrate is; and
providing a reaction material incorporated in the hollow-matrix conformation.

11. The manufacturing method of claim 10, wherein the channel further comprises a plurality of branch channels.

12. The manufacturing method of claim 11, wherein at least one said branch channel further comprises an extended region that has a shape selected from the group consisting of a dome, an oblong and an island.

13. The manufacturing method of claim 10, wherein the channel is made from a solution that is dried and solidified to form the hollow-matrix conformation, in which the solution is selected from the group consisting of nitrocellulose solution and fiberglass solution.

14. The manufacturing method of claim 10, wherein the reaction material is incorporated in the hollow-matrix conformation by injecting a reaction solution to the channel, and drying the reaction solution.

15. The manufacturing method of claim 10, wherein the reaction material is selected from the group consisting of a chemical reagent, an enzyme reagent, and an antibody.

16. The manufacturing method of claim 10, further comprising providing a pair of planar electrodes formed between the flat surface and the channel.

17. The manufacturing method of claim 10, further comprising providing a stacked channel formed on the channel.

18. A manufacturing method of an analytical strip, comprising:
- providing a substrate having a flat surface;
- providing a mask engraved with a pattern;
- adhering the mask detachably to the substrate;
- applying a solution into the engraved pattern;
- drying the applied solution;
- removing the mask to form a channel that has the pattern, in the manner that a surface of the channel is higher than the flat surface of the substrate, and the channel has a hollow-matrix conformation, wherein the channel is more hydrophilic than the flat surface of the substrate is; and
- providing a reaction material and incorporating the reaction material in the hollow-matrix conformation.

* * * * *